United States Patent
McCrea et al.

(10) Patent No.: US 10,660,713 B2
(45) Date of Patent: May 26, 2020

(54) WRIST AND JAW ASSEMBLIES FOR ROBOTIC SURGICAL SYSTEMS

(71) Applicant: Covidien LP, Mansfield, MA (US)

(72) Inventors: James McCrea, San Carlos, CA (US); Ruth Beeby, Santa Clara, CA (US); Thomas McGaffigan, Saratoga, CA (US); Steve Woodard, Cupertino, CA (US)

(73) Assignee: COVIDIEN LP, Mansfield, MA (US)

( * ) Notice: Subject to any disclaimer, the term of this patent is extended or adjusted under 35 U.S.C. 154(b) by 506 days.

(21) Appl. No.: 15/300,825

(22) PCT Filed: Dec. 5, 2014

(86) PCT No.: PCT/US2014/068705
§ 371 (c)(1),
(2) Date: Sep. 30, 2016

(87) PCT Pub. No.: WO2015/152972
PCT Pub. Date: Oct. 8, 2015

(65) Prior Publication Data
US 2017/0014197 A1   Jan. 19, 2017

Related U.S. Application Data

(60) Provisional application No. 61/972,607, filed on Mar. 31, 2014.

(51) Int. Cl.
*A61B 34/30* (2016.01)
*B25J 9/10* (2006.01)
(Continued)

(52) U.S. Cl.
CPC ............. *A61B 34/30* (2016.02); *A61B 34/71* (2016.02); *B25J 9/102* (2013.01); *B25J 9/104* (2013.01);
(Continued)

(58) Field of Classification Search
CPC ......... A61B 34/30; A61B 34/71; A61B 17/29; A61B 17/282; A61B 2034/306;
(Continued)

(56) References Cited

U.S. PATENT DOCUMENTS 2,777,340 A  1/1957  Hettwer et al.
2,957,353 A  10/1960  Babacz
(Continued)

FOREIGN PATENT DOCUMENTS

CA  2451558 A1  1/2003
CN  1547454 A  11/2004
(Continued)

OTHER PUBLICATIONS

Chinese First Office Action corresponding to counterpart Patent Appln. CN 2014800775465 dated Jul. 4, 2018.
(Continued)

*Primary Examiner* — Katrina M Stransky
*Assistant Examiner* — Brigid K Byrd

(57) ABSTRACT

An end effector for use and connection to a robot arm of a robotic surgical system, wherein the end effector is controlled and/or articulated by at least one cable extending from a respective motor of a control device of the robot surgical system, is provided. The end effector includes a jaw assembly defining a longitudinal axis and including a pair of jaws. Each jaw includes a proximal portion pivotally connected to the distal hub assembly; and a distal portion extending distally of the proximal portion thereof. The end effector additionally includes an actuation cable having a distal end operatively connected to the pair of jaws and a proximal end operatively connected to the at least one motor. In use, axial translation of the actuation cable results in one of an opening and a closing of the jaw assembly.

7 Claims, 5 Drawing Sheets

(51) Int. Cl.
*A61B 34/00* (2016.01)
*B25J 15/02* (2006.01)
(52) U.S. Cl.
CPC ......... *B25J 15/022* (2013.01); *B25J 15/0226* (2013.01); *A61B 2034/305* (2016.02)
(58) Field of Classification Search
CPC ..... A61B 17/28–295; A61B 2017/2932–2936; A61B 2017/2926–2929; A61B 2017/2912–2916; A61B 2034/305–306; B25J 9/102; B25J 9/104; B25J 15/022; B25J 15/0226
See application file for complete search history.

(56) References Cited

U.S. PATENT DOCUMENTS

| | | |
|---|---|---|
| 3,111,328 A | 11/1963 | Di Rito et al. |
| 3,695,058 A | 10/1972 | Keith, Jr. |
| 3,734,515 A | 5/1973 | Dudek |
| 3,759,336 A | 9/1973 | Marcovitz et al. |
| 4,162,399 A | 7/1979 | Hudson |
| 4,606,343 A | 8/1986 | Conta et al. |
| 4,705,038 A | 11/1987 | Sjostrom et al. |
| 4,722,685 A | 2/1988 | de Estrada et al. |
| 4,823,807 A | 4/1989 | Russell et al. |
| 4,874,181 A | 10/1989 | Hsu |
| 5,129,118 A | 7/1992 | Walmesley |
| 5,129,570 A | 7/1992 | Schulze et al. |
| 5,152,744 A | 10/1992 | Krause et al. |
| 5,301,061 A | 4/1994 | Nakada et al. |
| 5,312,023 A | 5/1994 | Green et al. |
| 5,326,013 A | 7/1994 | Green et al. |
| 5,350,355 A | 9/1994 | Sklar |
| 5,383,874 A | 1/1995 | Jackson et al. |
| 5,383,880 A | 1/1995 | Hooven |
| 5,389,098 A | 2/1995 | Tsuruta et al. |
| 5,395,033 A | 3/1995 | Byrne et al. |
| 5,400,267 A | 3/1995 | Denen et al. |
| 5,411,508 A | 5/1995 | Bessler et al. |
| 5,413,267 A | 5/1995 | Solyntjes et al. |
| 5,427,087 A | 6/1995 | Ito et al. |
| 5,433,721 A | 7/1995 | Hooven et al. |
| 5,467,911 A | 11/1995 | Tsuruta et al. |
| 5,476,379 A | 12/1995 | Disel |
| 5,487,499 A | 1/1996 | Sorrentino et al. |
| 5,518,163 A | 5/1996 | Hooven |
| 5,518,164 A | 5/1996 | Hooven |
| 5,526,822 A | 6/1996 | Burbank et al. |
| 5,529,235 A | 6/1996 | Boiarski et al. |
| 5,535,934 A | 7/1996 | Boiarski et al. |
| 5,535,937 A | 7/1996 | Boiarski et al. |
| 5,540,375 A | 7/1996 | Bolanos et al. |
| 5,540,706 A | 7/1996 | Aust et al. |
| 5,542,594 A | 8/1996 | McKean et al. |
| 5,549,637 A | 8/1996 | Crainich |
| 5,553,675 A | 9/1996 | Pitzen et al. |
| 5,562,239 A | 10/1996 | Boiarski et al. |
| 5,564,615 A | 10/1996 | Bishop et al. |
| 5,609,560 A | 3/1997 | Ichikawa et al. |
| 5,626,587 A | 5/1997 | Bishop et al. |
| 5,632,432 A | 5/1997 | Schulze et al. |
| 5,645,209 A | 7/1997 | Green et al. |
| 5,647,526 A | 7/1997 | Green et al. |
| 5,653,374 A | 8/1997 | Young et al. |
| 5,658,300 A | 8/1997 | Bito et al. |
| 5,662,662 A | 9/1997 | Bishop et al. |
| 5,667,517 A | 9/1997 | Hooven |
| 5,693,042 A | 12/1997 | Boiarski et al. |
| 5,704,534 A | 1/1998 | Huitema et al. |
| 5,713,505 A | 2/1998 | Huitema |
| 5,762,603 A | 6/1998 | Thompson |
| 5,779,130 A | 7/1998 | Alesi et al. |
| 5,782,396 A | 7/1998 | Mastri et al. |
| 5,782,397 A | 7/1998 | Koukline |
| 5,792,573 A | 8/1998 | Pitzen et al. |
| 5,797,536 A | 8/1998 | Smith et al. |
| 5,820,009 A | 10/1998 | Melling et al. |
| 5,863,159 A | 1/1999 | Lasko |
| 5,908,427 A | 6/1999 | McKean et al. |
| 5,954,259 A | 9/1999 | Viola et al. |
| 5,964,774 A | 10/1999 | McKean et al. |
| 5,993,454 A | 11/1999 | Longo |
| 6,010,054 A | 1/2000 | Johnson et al. |
| 6,017,354 A | 1/2000 | Culp et al. |
| 6,032,849 A | 3/2000 | Mastri et al. |
| 6,045,560 A | 4/2000 | McKean et al. |
| 6,090,123 A | 7/2000 | Culp et al. |
| 6,126,651 A | 10/2000 | Mayer |
| 6,129,547 A | 10/2000 | Cise et al. |
| 6,165,169 A | 12/2000 | Panescu et al. |
| 6,239,732 B1 | 5/2001 | Cusey |
| 6,241,139 B1 | 6/2001 | Milliman et al. |
| 6,264,086 B1 | 7/2001 | McGuckin, Jr. |
| 6,264,087 B1 | 7/2001 | Whitman |
| 6,302,311 B1 | 10/2001 | Adams et al. |
| 6,315,184 B1 | 11/2001 | Whitman |
| 6,321,855 B1 | 11/2001 | Barnes |
| 6,329,778 B1 | 12/2001 | Culp et al. |
| 6,343,731 B1 | 2/2002 | Adams et al. |
| 6,348,061 B1 | 2/2002 | Whitman |
| 6,368,324 B1 | 4/2002 | Dinger et al. |
| 6,371,909 B1 | 4/2002 | Hoeg et al. |
| 6,434,507 B1 | 8/2002 | Clayton et al. |
| 6,443,973 B1 | 9/2002 | Whitman |
| 6,461,372 B1 | 10/2002 | Jensen et al. |
| 6,488,197 B1 | 12/2002 | Whitman |
| 6,491,201 B1 | 12/2002 | Whitman |
| 6,533,157 B1 | 3/2003 | Whitman |
| 6,537,280 B2 | 3/2003 | Dinger et al. |
| 6,610,066 B2 | 8/2003 | Dinger et al. |
| 6,611,793 B1 | 8/2003 | Burnside et al. |
| 6,645,218 B1 | 11/2003 | Cassidy et al. |
| 6,654,999 B2 | 12/2003 | Stoddard et al. |
| 6,663,641 B1 | 12/2003 | Kovac et al. |
| 6,698,643 B2 | 3/2004 | Whitman |
| 6,699,177 B1 | 3/2004 | Wang et al. |
| 6,716,233 B1 | 4/2004 | Whitman |
| 6,743,240 B2 | 6/2004 | Smith et al. |
| 6,783,533 B2 | 8/2004 | Green et al. |
| 6,792,390 B1 | 9/2004 | Burnside et al. |
| 6,793,652 B1 | 9/2004 | Whitman et al. |
| 6,817,508 B1 | 11/2004 | Racenet et al. |
| 6,830,174 B2 | 12/2004 | Hillstead et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,860,892 B1 | 3/2005 | Tanaka et al. |
| 6,899,538 B2 | 5/2005 | Matoba |
| 6,905,057 B2 | 6/2005 | Swayze et al. |
| 6,959,852 B2 | 11/2005 | Shelton, IV et al. |
| 6,964,363 B2 | 11/2005 | Wales et al. |
| 6,969,385 B2 | 11/2005 | Moreyra |
| 6,981,628 B2 | 1/2006 | Wales |
| 6,981,941 B2 | 1/2006 | Whitman et al. |
| 6,986,451 B1 | 1/2006 | Mastri et al. |
| 6,988,649 B2 | 1/2006 | Shelton, IV et al. |
| 7,032,798 B2 | 4/2006 | Whitman et al. |
| RE39,152 E | 6/2006 | Aust et al. |
| 7,055,731 B2 | 6/2006 | Shelton, IV et al. |
| 7,059,508 B2 | 6/2006 | Shelton, IV et al. |
| 7,077,856 B2 | 7/2006 | Whitman |
| 7,083,618 B2 * | 8/2006 | Couture ............. A61B 18/1445 606/51 |
| 7,111,769 B2 | 9/2006 | Wales et al. |
| 7,122,029 B2 | 10/2006 | Koop et al. |
| 7,140,528 B2 | 11/2006 | Shelton, IV |
| 7,141,049 B2 | 11/2006 | Stern et al. |
| 7,143,923 B2 | 12/2006 | Shelton, IV et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,172,104 B2 | 2/2007 | Scirica et al. |
| 7,225,964 B2 | 6/2007 | Mastri et al. |

(56) References Cited

U.S. PATENT DOCUMENTS

| | | |
|---|---|---|
| 7,238,021 B1 | 7/2007 | Johnson |
| 7,246,734 B2 | 7/2007 | Shelton, IV |
| 7,252,660 B2 | 8/2007 | Kunz |
| 7,328,828 B2 | 2/2008 | Ortiz et al. |
| 7,364,061 B2 | 4/2008 | Swayze |
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,422,139 B2 | 9/2008 | Shelton, IV et al. |
| 7,431,189 B2 | 10/2008 | Shelton, IV et al. |
| 7,441,684 B2 | 10/2008 | Shelton, IV et al. |
| 7,448,525 B2 | 11/2008 | Shelton, IV et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,481,347 B2 | 1/2009 | Roy |
| 7,481,824 B2 | 1/2009 | Boudreaux et al. |
| 7,487,899 B2 | 2/2009 | Shelton, IV et al. |
| 7,549,564 B2 | 6/2009 | Boudreaux |
| 7,565,993 B2 | 7/2009 | Milliman et al. |
| 7,568,603 B2 | 8/2009 | Shelton, IV et al. |
| 7,575,144 B2 | 8/2009 | Ortiz et al. |
| 7,588,175 B2 | 9/2009 | Timm et al. |
| 7,588,176 B2 | 9/2009 | Timm et al. |
| 7,637,409 B2 | 12/2009 | Marczyk |
| 7,641,093 B2 | 1/2010 | Doll et al. |
| 7,644,848 B2 | 1/2010 | Swayze et al. |
| 7,670,334 B2 | 3/2010 | Hueil et al. |
| 7,673,780 B2 | 3/2010 | Shelton, IV et al. |
| 7,699,835 B2 | 4/2010 | Lee et al. |
| 7,721,931 B2 | 5/2010 | Shelton, IV et al. |
| 7,738,971 B2 | 6/2010 | Swayze et al. |
| 7,740,159 B2 | 6/2010 | Shelton, IV et al. |
| 7,743,960 B2 | 6/2010 | Whitman et al. |
| 7,758,613 B2 | 7/2010 | Whitman |
| 7,766,210 B2 | 8/2010 | Shelton, IV et al. |
| 7,770,773 B2 | 8/2010 | Whitman et al. |
| 7,770,775 B2 | 8/2010 | Shelton, IV et al. |
| 7,793,812 B2 | 9/2010 | Moore et al. |
| 7,799,039 B2 | 9/2010 | Shelton, IV et al. |
| 7,802,712 B2 | 9/2010 | Milliman et al. |
| 7,803,151 B2 | 9/2010 | Whitman |
| 7,822,458 B2 | 10/2010 | Webster, III et al. |
| 7,845,534 B2 | 12/2010 | Viola et al. |
| 7,845,537 B2 | 12/2010 | Shelton, IV et al. |
| 7,857,185 B2 | 12/2010 | Swayze |
| 7,870,989 B2 | 1/2011 | Viola et al. |
| 7,900,805 B2 | 3/2011 | Shelton, IV et al. |
| 7,905,897 B2 | 3/2011 | Whitman et al. |
| 7,918,230 B2 | 4/2011 | Whitman et al. |
| 7,922,061 B2 | 4/2011 | Shelton, IV et al. |
| 7,922,719 B2 | 4/2011 | Ralph et al. |
| 7,947,034 B2 | 5/2011 | Whitman |
| 7,951,071 B2 | 5/2011 | Whitman et al. |
| 7,954,682 B2 | 6/2011 | Giordano et al. |
| 7,959,051 B2 | 6/2011 | Smith et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,992,758 B2 | 8/2011 | Whitman et al. |
| 8,011,550 B2 | 9/2011 | Aranyi et al. |
| 8,016,178 B2 | 9/2011 | Olson et al. |
| 8,016,855 B2 | 9/2011 | Whitman et al. |
| 8,020,743 B2 | 9/2011 | Shelton, IV |
| 8,025,199 B2 | 9/2011 | Whitman et al. |
| 8,035,487 B2 | 10/2011 | Malackowski |
| 8,052,024 B2 | 11/2011 | Viola et al. |
| 8,074,859 B2 | 12/2011 | Kostrzewski |
| 8,114,118 B2 | 2/2012 | Knodel et al. |
| 8,127,975 B2 | 3/2012 | Olson et al. |
| 8,132,705 B2 | 3/2012 | Viola et al. |
| 8,152,516 B2 | 4/2012 | Harvey et al. |
| 8,157,150 B2 | 4/2012 | Viola et al. |
| 8,157,151 B2 | 4/2012 | Ingmanson et al. |
| 8,182,494 B1 | 5/2012 | Yencho et al. |
| 8,186,555 B2 | 5/2012 | Shelton, IV et al. |
| 8,186,587 B2 | 5/2012 | Zmood et al. |
| 8,220,367 B2 | 7/2012 | Hsu |
| 8,235,273 B2 | 8/2012 | Olson et al. |
| 8,241,322 B2 | 8/2012 | Whitman et al. |
| 8,272,554 B2 | 9/2012 | Whitman et al. |
| 8,292,150 B2 | 10/2012 | Bryant |
| 8,292,888 B2 | 10/2012 | Whitman |
| 8,342,379 B2 | 1/2013 | Whitman et al. |
| 8,348,130 B2 | 1/2013 | Shah et al. |
| 8,348,855 B2 | 1/2013 | Hillely et al. |
| 8,353,440 B2 | 1/2013 | Whitman et al. |
| 8,357,144 B2 | 1/2013 | Whitman et al. |
| 8,365,633 B2 | 2/2013 | Simaan et al. |
| 8,365,972 B2 | 2/2013 | Aranyi et al. |
| 8,371,492 B2 | 2/2013 | Aranyi et al. |
| 8,372,057 B2 | 2/2013 | Cude et al. |
| 8,391,957 B2 | 3/2013 | Carlson et al. |
| 8,398,619 B2 | 3/2013 | Doyle et al. |
| 8,403,926 B2 | 3/2013 | Nobis et al. |
| 8,418,904 B2 | 4/2013 | Wenchell et al. |
| 8,424,739 B2 | 4/2013 | Racenet et al. |
| 8,454,585 B2 | 6/2013 | Whitman |
| 8,505,802 B2 | 8/2013 | Viola et al. |
| 8,517,241 B2 | 8/2013 | Nicholas et al. |
| 8,523,043 B2 | 9/2013 | Ullrich et al. |
| 8,551,076 B2 | 10/2013 | Duval et al. |
| 8,561,871 B2 | 10/2013 | Rajappa et al. |
| 8,561,874 B2 | 10/2013 | Scirica |
| 8,602,287 B2 | 12/2013 | Yates et al. |
| 8,617,203 B2 | 12/2013 | Stefanchik et al. |
| 8,623,000 B2 | 1/2014 | Humayun et al. |
| 8,627,995 B2 | 1/2014 | Smith et al. |
| 8,632,463 B2 | 1/2014 | Drinan et al. |
| 8,636,766 B2 | 1/2014 | Milliman et al. |
| 8,647,258 B2 | 2/2014 | Aranyi et al. |
| 8,652,121 B2 | 2/2014 | Quick et al. |
| 8,657,174 B2 | 2/2014 | Yates et al. |
| 8,657,177 B2 | 2/2014 | Scirica et al. |
| 8,672,206 B2 | 3/2014 | Aranyi et al. |
| 8,696,552 B2 | 4/2014 | Whitman |
| 8,708,213 B2 | 4/2014 | Shelton, IV et al. |
| 8,715,306 B2 | 5/2014 | Faller et al. |
| 8,758,391 B2 | 6/2014 | Swayze et al. |
| 8,806,973 B2 | 8/2014 | Ross et al. |
| 8,808,311 B2 | 8/2014 | Heinrich et al. |
| 8,820,605 B2 | 9/2014 | Shelton, IV |
| 8,851,355 B2 | 10/2014 | Aranyi et al. |
| 8,858,571 B2 | 10/2014 | Shelton, IV et al. |
| 8,875,972 B2 | 11/2014 | Weisenburgh, II et al. |
| 8,888,762 B2 | 11/2014 | Whitman |
| 8,893,946 B2 | 11/2014 | Boudreaux et al. |
| 8,899,462 B2 | 12/2014 | Kostrzewski et al. |
| 8,905,289 B2 | 12/2014 | Patel et al. |
| 8,919,630 B2 | 12/2014 | Milliman |
| 8,931,680 B2 | 1/2015 | Milliman |
| 8,939,344 B2 | 1/2015 | Olson et al. |
| 8,950,646 B2 | 2/2015 | Viola |
| 8,960,519 B2 | 2/2015 | Whitman et al. |
| 8,961,396 B2 | 2/2015 | Azarbarzin et al. |
| 8,967,443 B2 | 3/2015 | McCuen |
| 8,968,276 B2 | 3/2015 | Zemlok et al. |
| 8,968,337 B2 | 3/2015 | Whitfield et al. |
| 8,992,422 B2 | 3/2015 | Spivey et al. |
| 9,016,545 B2 | 4/2015 | Aranyi et al. |
| 9,023,014 B2 | 5/2015 | Chowaniec et al. |
| 9,033,868 B2 | 5/2015 | Whitman et al. |
| 9,055,943 B2 | 6/2015 | Zemlok et al. |
| 9,064,653 B2 | 6/2015 | Prest et al. |
| 9,072,515 B2 | 7/2015 | Hall et al. |
| 9,113,847 B2 | 8/2015 | Whitman et al. |
| 9,113,875 B2 | 8/2015 | Viola et al. |
| 9,113,876 B2 | 8/2015 | Zemlok et al. |
| 9,113,899 B2 | 8/2015 | Garrison et al. |
| 9,216,013 B2 | 12/2015 | Scirica et al. |
| 9,241,712 B2 | 1/2016 | Zemlok et al. |

(56) References Cited

U.S. PATENT DOCUMENTS

| | | | |
|---|---|---|---|
| 9,282,961 B2 | 3/2016 | Whitman et al. |
| 9,282,963 B2 | 3/2016 | Bryant |
| 9,295,522 B2 | 3/2016 | Kostrzewski |
| 9,307,986 B2 | 4/2016 | Hall et al. |
| 2001/0031975 A1 | 10/2001 | Whitman et al. |
| 2002/0049454 A1 | 4/2002 | Whitman et al. |
| 2002/0165541 A1 | 11/2002 | Whitman |
| 2003/0038938 A1 | 2/2003 | Jung et al. |
| 2003/0165794 A1 | 9/2003 | Matoba |
| 2004/0034369 A1 | 2/2004 | Sauer et al. |
| 2004/0111012 A1 | 6/2004 | Whitman |
| 2004/0133189 A1 | 7/2004 | Sakurai |
| 2004/0153124 A1 | 8/2004 | Whitman |
| 2004/0176751 A1 | 9/2004 | Weitzner et al. |
| 2004/0193146 A1 | 9/2004 | Lee et al. |
| 2004/0260336 A1 | 12/2004 | Braun |
| 2005/0125027 A1 | 6/2005 | Knodel et al. |
| 2005/0131442 A1 | 6/2005 | Yachia et al. |
| 2006/0074415 A1 | 4/2006 | Scott et al. |
| 2006/0142656 A1 | 6/2006 | Malackowski et al. |
| 2006/0142740 A1 | 6/2006 | Sherman et al. |
| 2006/0142744 A1 | 6/2006 | Boutoussov |
| 2006/0259073 A1 | 11/2006 | Miyamoto et al. |
| 2006/0278680 A1 | 12/2006 | Viola et al. |
| 2006/0284730 A1 | 12/2006 | Schmid et al. |
| 2007/0023476 A1 | 2/2007 | Whitman et al. |
| 2007/0023477 A1 | 2/2007 | Whitman et al. |
| 2007/0029363 A1 | 2/2007 | Popov |
| 2007/0084897 A1 | 4/2007 | Shelton et al. |
| 2007/0102472 A1 | 5/2007 | Shelton |
| 2007/0152014 A1 | 7/2007 | Gillum et al. |
| 2007/0175947 A1 | 8/2007 | Ortiz et al. |
| 2007/0175949 A1 | 8/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0175961 A1 | 8/2007 | Shelton et al. |
| 2007/0270784 A1 | 11/2007 | Smith et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0058801 A1 | 3/2008 | Taylor et al. |
| 2008/0108443 A1 | 5/2008 | Jinno et al. |
| 2008/0109012 A1 | 5/2008 | Falco et al. |
| 2008/0110958 A1 | 5/2008 | McKenna et al. |
| 2008/0147089 A1 | 6/2008 | Loh et al. |
| 2008/0167736 A1 | 7/2008 | Swayze et al. |
| 2008/0185419 A1 | 8/2008 | Smith et al. |
| 2008/0188841 A1 | 8/2008 | Tomasello et al. |
| 2008/0197167 A1 | 8/2008 | Viola et al. |
| 2008/0208195 A1 | 8/2008 | Shores et al. |
| 2008/0237296 A1 | 10/2008 | Boudreaux et al. |
| 2008/0251561 A1 | 10/2008 | Eades et al. |
| 2008/0255413 A1 | 10/2008 | Zemlok et al. |
| 2008/0255607 A1 | 10/2008 | Zemlok |
| 2008/0262654 A1 | 10/2008 | Omori et al. |
| 2008/0308603 A1 | 12/2008 | Shelton et al. |
| 2009/0012533 A1 | 1/2009 | Barbagli et al. |
| 2009/0090763 A1 | 4/2009 | Zemlok et al. |
| 2009/0099876 A1 | 4/2009 | Whitman |
| 2009/0138006 A1 | 5/2009 | Bales et al. |
| 2009/0171147 A1 | 7/2009 | Lee et al. |
| 2009/0182193 A1 | 7/2009 | Whitman et al. |
| 2009/0209946 A1 | 8/2009 | Swayze et al. |
| 2009/0209990 A1 | 8/2009 | Yates et al. |
| 2009/0254094 A1 | 10/2009 | Knapp et al. |
| 2009/0299141 A1 | 12/2009 | Downey et al. |
| 2009/0299143 A1 | 12/2009 | Conlon et al. |
| 2010/0010512 A1 | 1/2010 | Taylor et al. |
| 2010/0023022 A1 | 1/2010 | Zeiner et al. |
| 2010/0069942 A1 | 3/2010 | Shelton, IV |
| 2010/0193568 A1 | 8/2010 | Scheib et al. |
| 2010/0211053 A1 | 8/2010 | Ross et al. |
| 2010/0225073 A1 | 9/2010 | Porter et al. |
| 2011/0071508 A1 | 3/2011 | Duval et al. |
| 2011/0077673 A1 | 3/2011 | Grubac et al. |
| 2011/0106145 A1 | 5/2011 | Jeong |
| 2011/0121049 A1 | 5/2011 | Malinouskas et al. |
| 2011/0125138 A1 | 5/2011 | Malinouskas et al. |
| 2011/0139851 A1 | 6/2011 | McCuen |
| 2011/0155783 A1 | 6/2011 | Rajappa et al. |
| 2011/0155786 A1 | 6/2011 | Shelton, IV |
| 2011/0172648 A1 | 7/2011 | Jeong |
| 2011/0174009 A1 | 7/2011 | Iizuka et al. |
| 2011/0174099 A1 | 7/2011 | Ross et al. |
| 2011/0184245 A1 | 7/2011 | Xia et al. |
| 2011/0184459 A1* | 7/2011 | Malkowski ............ A61B 17/29 |
| | | 606/206 |
| 2011/0204119 A1 | 8/2011 | McCuen |
| 2011/0218522 A1 | 9/2011 | Whitman |
| 2011/0238064 A1 | 9/2011 | Williams |
| 2011/0276057 A1 | 11/2011 | Conlon et al. |
| 2011/0290854 A1 | 12/2011 | Timm et al. |
| 2011/0295242 A1 | 12/2011 | Spivey et al. |
| 2011/0295269 A1 | 12/2011 | Swensgard et al. |
| 2011/0301637 A1 | 12/2011 | Kerr et al. |
| 2012/0000962 A1 | 1/2012 | Racenet et al. |
| 2012/0074199 A1 | 3/2012 | Olson et al. |
| 2012/0080475 A1 | 4/2012 | Smith et al. |
| 2012/0089131 A1 | 4/2012 | Zemlok et al. |
| 2012/0104071 A1 | 5/2012 | Bryant |
| 2012/0116368 A1 | 5/2012 | Viola |
| 2012/0116416 A1 | 5/2012 | Neff et al. |
| 2012/0143002 A1 | 6/2012 | Aranyi et al. |
| 2012/0158013 A1 | 6/2012 | Stefanchik et al. |
| 2012/0172924 A1 | 7/2012 | Allen, IV |
| 2012/0211542 A1 | 8/2012 | Racenet |
| 2012/0223121 A1 | 9/2012 | Viola et al. |
| 2012/0245428 A1 | 9/2012 | Smith et al. |
| 2012/0253329 A1 | 10/2012 | Zemlok et al. |
| 2012/0310220 A1 | 12/2012 | Malkowski et al. |
| 2012/0323226 A1 | 12/2012 | Chowaniec et al. |
| 2012/0330285 A1 | 12/2012 | Hartoumbekis et al. |
| 2013/0093149 A1 | 4/2013 | Saur et al. |
| 2013/0110131 A1 | 5/2013 | Madhani et al. |
| 2013/0123783 A1 | 5/2013 | Marczyk et al. |
| 2013/0181035 A1 | 7/2013 | Milliman |
| 2013/0184704 A1 | 7/2013 | Beardsley et al. |
| 2013/0214025 A1 | 8/2013 | Zemlok et al. |
| 2013/0274722 A1 | 10/2013 | Kostrzewski et al. |
| 2013/0282052 A1 | 10/2013 | Aranyi et al. |
| 2013/0292451 A1 | 11/2013 | Viola et al. |
| 2013/0313304 A1 | 11/2013 | Shelton, IV et al. |
| 2013/0317486 A1 | 11/2013 | Nicholas et al. |
| 2013/0319706 A1 | 12/2013 | Nicholas et al. |
| 2013/0324978 A1 | 12/2013 | Nicholas et al. |
| 2013/0324979 A1 | 12/2013 | Nicholas et al. |
| 2013/0334281 A1 | 12/2013 | Williams |
| 2014/0005653 A1* | 1/2014 | Shelton, IV ........ A61B 18/1442 |
| | | 606/33 |
| 2014/0012236 A1 | 1/2014 | Williams et al. |
| 2014/0012237 A1 | 1/2014 | Pribanic et al. |
| 2014/0012289 A1 | 1/2014 | Snow et al. |
| 2014/0025046 A1 | 1/2014 | Williams et al. |
| 2014/0110455 A1 | 4/2014 | Ingmanson et al. |
| 2014/0188159 A1* | 7/2014 | Steege ................... A61B 17/29 |
| | | 606/207 |
| 2014/0207125 A1 | 7/2014 | Applegate et al. |
| 2014/0207182 A1 | 7/2014 | Zergiebel et al. |
| 2014/0207185 A1 | 7/2014 | Goble et al. |
| 2014/0236174 A1 | 8/2014 | Williams et al. |
| 2014/0276932 A1 | 9/2014 | Williams et al. |
| 2014/0299647 A1 | 10/2014 | Scirica et al. |
| 2014/0303668 A1 | 10/2014 | Nicholas et al. |
| 2014/0358129 A1 | 12/2014 | Zergiebel et al. |
| 2014/0361068 A1 | 12/2014 | Aranyi et al. |
| 2014/0365235 A1 | 12/2014 | DeBoer et al. |
| 2014/0373652 A1 | 12/2014 | Zergiebel et al. |
| 2015/0014392 A1 | 1/2015 | Williams et al. |
| 2015/0048144 A1 | 2/2015 | Whitman |
| 2015/0076205 A1 | 3/2015 | Zergiebel |
| 2015/0080912 A1 | 3/2015 | Sapre |
| 2015/0112381 A1 | 4/2015 | Richard |

(56) References Cited

U.S. PATENT DOCUMENTS

| | | | |
|---|---|---|---|
| 2015/0122870 A1 | 5/2015 | Zemlok et al. |
| 2015/0133224 A1 | 5/2015 | Whitman et al. |
| 2015/0150547 A1 | 6/2015 | Ingmanson et al. |
| 2015/0150574 A1 | 6/2015 | Richard et al. |
| 2015/0157320 A1 | 6/2015 | Zergiebel et al. |
| 2015/0157321 A1 | 6/2015 | Zergiebel et al. |
| 2015/0164502 A1 | 6/2015 | Richard et al. |
| 2015/0201931 A1 | 7/2015 | Zergiebel et al. |
| 2015/0272577 A1 | 10/2015 | Zemlok et al. |
| 2015/0297199 A1 | 10/2015 | Nicholas et al. |
| 2015/0303996 A1 | 10/2015 | Calderoni |
| 2015/0320420 A1 | 11/2015 | Penna et al. |
| 2015/0327850 A1 | 11/2015 | Kostrzewski |
| 2015/0342601 A1 | 12/2015 | Williams et al. |
| 2015/0342603 A1 | 12/2015 | Zergiebel et al. |
| 2015/0374366 A1 | 12/2015 | Zergiebel et al. |
| 2015/0374370 A1 | 12/2015 | Zergiebel et al. |
| 2015/0374371 A1 | 12/2015 | Richard et al. |
| 2015/0374372 A1 | 12/2015 | Zergiebel et al. |
| 2015/0374449 A1 | 12/2015 | Chowaniec et al. |
| 2015/0380187 A1 | 12/2015 | Zergiebel et al. |
| 2016/0095585 A1 | 4/2016 | Zergiebel et al. |
| 2016/0095596 A1 | 4/2016 | Scirica et al. |
| 2016/0106406 A1 | 4/2016 | Cabrera et al. |
| 2016/0113648 A1 | 4/2016 | Zergiebel et al. |
| 2016/0113649 A1 | 4/2016 | Zergiebel et al. |
| 2016/0303743 A1* | 10/2016 | Rockrohr | B25J 15/0226 |

FOREIGN PATENT DOCUMENTS

| | | |
|---|---|---|
| CN | 1957854 A | 5/2007 |
| CN | 101495046 A | 7/2009 |
| CN | 102084141 A | 6/2011 |
| CN | 102247182 A | 11/2011 |
| DE | 102008053842 A1 | 5/2010 |
| EP | 0705571 A1 | 4/1996 |
| EP | 1563793 A1 | 8/2005 |
| EP | 1769754 A1 | 4/2007 |
| EP | 2316345 A1 | 5/2011 |
| EP | 2668910 A2 | 12/2013 |
| ES | 2333509 A1 | 2/2010 |
| JP | 2005-125075 A | 5/2005 |
| KR | 20120022521 A | 3/2012 |
| WO | 2011/108840 A2 | 9/2011 |
| WO | 2011-115310 A1 | 9/2011 |
| WO | 2012/040984 A1 | 4/2012 |
| WO | WO2013/158974 | 10/2013 |
| WO | 2015-122943 A1 | 8/2015 |

OTHER PUBLICATIONS

International Search Report & Written Opinion corresponding to counterpart Int'l Appln. No. PCT/US2014/064006 dated Feb. 5, 2015.
International Search Report & Written Opinion corresponding to counterpart Int'l Appln. No. PCT/US2014/064009 dated Feb. 5, 2015.
Extended European Search Report corresponding to counterpart International Application No. EP 14 18 4882.0 dated May 12, 2015.
Canadian Office Action corresponding to counterpart International Application No. CA 2640399 dated May 7, 2015.
Japanese Office Action corresponding to counterpart International Application No. JP 2011-197365 dated Mar. 23, 2015.
Japanese Office Action corresponding to counterpart International Application No. JP 2011-084092 dated May 20, 2015.
Japanese Office Action corresponding to counterpart International Application No. JP 2014-148482 dated Jun. 2, 2015.
Extended European Search Report corresponding to counterpart International Application No. EP 14 18 9358.6 dated Jul. 8, 2015.
Extended European Search Report corresponding to counterpart International Application No. EP 14 19 6148.2 dated Apr. 23, 2015.
Partial European Search Report corresponding to counterpart International Application No. EP 14 19 6704.2 dated May 11, 2015.
Australian Office Action corresponding to counterpart International Application No. AU 2010241367 dated Aug. 20, 2015.
Partial European Search Report corresponding to counterpart International Application No. EP 14 19 9783.3 dated Sep. 3, 2015.
Extended European Search Report corresponding to counterpart International Application No. EP 15 16 9962.6 dated Sep. 14, 2015.
Extended European Search Report corresponding to International Application No. EP 15 15 1076.5 dated Apr. 22, 2015.
Japanese Office Action corresponding to International Application No. JP 2011-084092 dated Jan. 14, 2016.
Extended European Search Report corresponding to International Application No. EP 12 19 7970.2 dated Jan. 28, 2016.
Chinese Office Action corresponding to International Application No. CN 201210560638.1 dated Oct. 21, 2015.
European Office Action corresponding to International Application No. EP 14 15 9056.2 dated Oct. 26, 2015.
Australian Examination Report No. 1 corresponding to International Application No. AU 2015200153 dated Dec. 11, 2015.
Australian Examination Report No. 1 corresponding to International Application No. AU 2014204542 dated Jan. 7, 2016.
Chinese Office Action corresponding to International Application No. CN 201310125449.6 dated Feb. 3, 2016.
Extended European Search Report corresponding to International Application No. EP 15 19 0245.9 dated Jan. 28, 2016.
Extended European Search Report corresponding to International Application No. EP 15 16 7793.7 dated Apr. 5, 2016.
European Office Action corresponding to International Application No. EP 14 18 4882.0 dated Apr. 25, 2016.
Extended European Search Report corresponding to International Application No. EP 14 19 6704.2 dated Sep. 24, 2015.
International Search Report and Written Opinion corresponding to Int'l Appln. No. PCT/US2015/051837, dated Dec. 21, 2015.
Extended European Search Report corresponding to International Application No. EP 14 19 7563.1 dated Aug. 5, 2015.
Partial European Search Report corresponding to International Application No. EP 15 19 0643.5 dated Feb. 26, 2016.
Extended European Search Report corresponding to International Application No. EP 15 16 6899.3 dated Feb. 3, 2016.
Extended European Search Report corresponding to International Application No. EP 14 19 9783.3 dated Dec. 22, 2015.
Extended European Search Report corresponding to International Application No. EP 15 17 3807.7 dated Nov. 24, 2015.
Extended European Search Report corresponding to International Application No. EP 15 19 0760.7 dated Apr. 1, 2016.
Extended European Search Report corresponding to International Application No. EP 15 17 3803.6 dated Nov. 24, 2015.
Extended European Search Report corresponding to International Application No. EP 15 17 3804.4 dated Nov. 24, 2015.
Extended European Search Report corresponding to International Application No. EP 15 18 8539.9 dated Feb. 17, 2016.
Extended European Search Report corresponding to International Application No. EP 15 17 3910.9 dated Nov. 13, 2015.
European Office Action corresponding to International Application No. EP 14 15 2236.7 dated Aug. 11, 2015.
Extended European Search Report corresponding to International Application No. EP 15 18 4915.5 dated Jan. 5, 2016.
Chinese Office Action corresponding to counterpart Int'l Appln. No. CN 201310369318.2 dated Jun. 28, 2016.
Chinese Office Action (with English translation), dated Jul. 4, 2016, corresponding to Chinese Patent Application No. 2013101559718; 23 total pages.
International Search Report corresponding to PCT/US2014/061329 dated Jan. 28, 2015.
International Search Report for (PCT/US2014/068705) date of completion is Mar. 12, 2015 (5 pages).
European Office Action corresponding to counterpart Patent Application EP 14887842.4 dated Jan. 28, 2019.
Chinese Second Office Action corresponding to counterpart Patent Appln. CN 201480077546.5 dated Mar. 11, 2019.

* cited by examiner

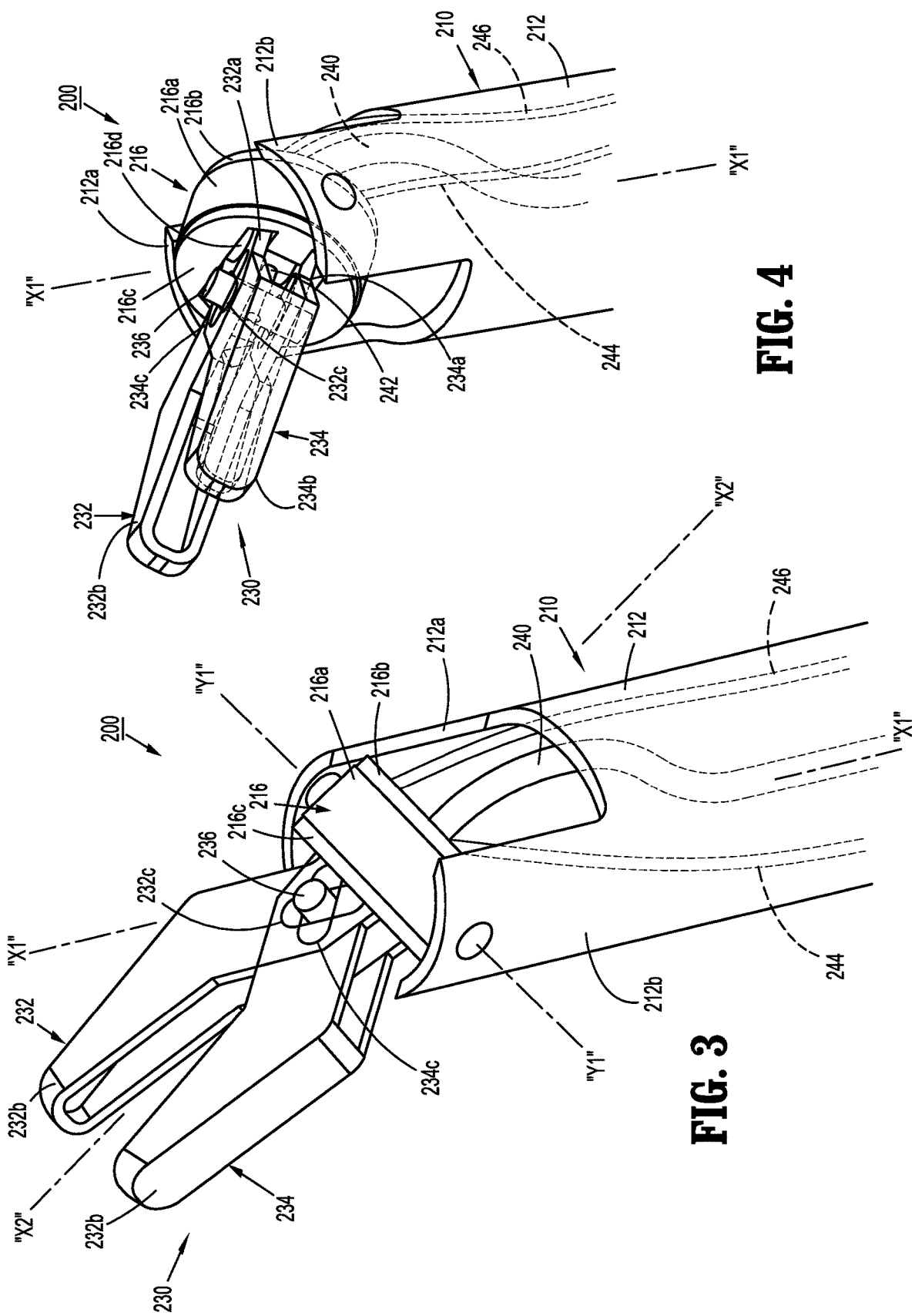

WRIST AND JAW ASSEMBLIES FOR ROBOTIC SURGICAL SYSTEMS

CROSS-REFERENCE TO RELATED APPLICATIONS

This application is a U.S. National Stage Application filed under 35 U.S.C. § 371(a) of International Patent Application Serial No. PCT/US2014/068705, filed Dec. 5, 2014, which claimed benefit of, and priority to, U.S. Provisional Patent Application Ser. No. 61/972,607, filed on Mar. 31, 2014. The entire contents of each of the above applications are hereby incorporated by reference.

BACKGROUND

Robotic surgical systems have been used in minimally invasive medical procedures. Some robotic surgical systems included a console supporting a robot arm, and at least one end effector such as forceps or a grasping tool that is mounted to the robot arm via a wrist assembly. During a medical procedure, the end effector and the wrist assembly were inserted into a small incision (via a cannula) or a natural orifice of a patient to position the end effector at a work site within the body of the patient.

Cables were extended from the robot console, through the robot arm, and connected to the wrist assembly and/or end effector. In some instances, the cables were actuated by means of motors that were controlled by a processing system including a user interface for a surgeon or clinician to be able to control the robotic surgical system including the robot arm, the wrist assembly and/or the end effector.

In some instances, the wrist assembly provided three degrees of freedom for movement of the end effector through the use of three cables or cable pairs, one for each degree of freedom. For example, for grasping or cutting end effectors the wrist assembly provided the three degrees of freedom by allowing changes to a pitch, a yaw, and an opening and closing of the end effector.

As demand for smaller surgical tools increased, device manufacturers developed surgical tools such as grasping and cutting tools having smaller cross-sectional areas. These smaller cross-sectional areas reduced the total force that could be applied between two jaws at the end of the tools. Additionally, the use of three cables or cable pairs to provide three degrees of motion required a minimum cross-sectional area to implement and limit the ability to further reduce the cross sectional area of these tools. Finally, the force that was applied was not customizable to provide varying forces depending on the position of the jaws in relation to each other as the jaws are opened and closed.

There is a need for surgical tools having relatively small cross-sectional areas and relatively shorter lengths that are able to provide high forces between end effector jaws.

SUMMARY

Jaws at the end of surgical robotics tools, such as foreceps or scissor cutting tools, may be driven by a cable/tube and gear system. In some instances, the cable/tube and gear system may be driven directly so at least one cable/tube controls a pitch, at least one cable/tube controls a yaw, and at least one cable/tube opens and closes the jaws.

End effectors, including wrist assemblies and jaw assemblies, may be used with and actuated by robotic surgical systems. In some instances, an end effector may be controlled and/or articulated by at least one cable/tube extending from a respective motor of a control device of the robot surgical system.

According to one aspect of the present disclosure, an end effector for use and connection to a robot arm of a robotic surgical system is provided, wherein the end effector is controlled and/or articulated by at least one motor of a control device of the robot surgical system. The end effector includes a wrist assembly defining a longitudinal axis. The wrist assembly including at least one support; and a distal hub assembly pivotally connected to the at least one support about a pivot axis.

The end effector further includes a jaw assembly defining a longitudinal axis and including a pair of jaws. Each jaw includes a proximal portion pivotally connected to the distal hub assembly; and a distal portion extending distally of the proximal portion thereof.

The end effector additionally includes an actuation cable having a distal end operatively connected to the pair of jaws and a proximal end operatively connected to the at least one motor. In use, axial translation of the actuation cable results in one of an opening and a closing of the jaw assembly.

The end effector may further include a torque transmitting tube having a distal end operatively connected to the jaw assembly and a proximal end operatively connected to a respective motor of the at least one motor. Rotation of the torque transmitting tube may result in rotation of the jaw assembly about the longitudinal axis thereof.

The jaw assembly may include a link arm extending from each jaw. Each link arm may be connected to the actuation cable.

The torque transmitting tube may define a lumen therethrough. The actuation cable may be is disposed within the lumen of the torque transmitting tube.

The distal hub assembly may include a body portion defining a distal recess including a ring of gear teeth formed in a surface thereof; a sun gear rotatably supported in the distal recess of the body portion, wherein the sub gear in non-rotatably connected to the distal end of the torque transmitting tube; and a pair of planet gears rotatably supported in the distal recess of the body portion. The planet gears may be interposed between and in meshing engagement with the ring of gear teeth of the body portion and the sun gear. Each jaw may be pivotally connected to a respective planet gear.

Each planet gear may be supported on a respective planet gear shaft. Each jaw may be pivotally connected to a respective planet gear shaft.

The end effector may further include a pair of articulation cables operatively connected to the distal hub assembly. A distal end of each articulation cable may be spaced an opposed radial distance from the pivot axis.

Each jaw of the pair of jaws may define an angled slot therein. The actuation cable may support a cam pin at a distal end thereof, wherein the cam pin may be slidably disposed within the angled slots defined in each jaw.

The distal hub assembly may include a cylindrical body pivotally connected to the at least one support. The jaw assembly may be supported in the distal hub assembly so as to be rotatable about a central axis of the cylindrical body and relative to the cylindrical body.

The pair of jaws may be pivotally supported in the cylindrical body so as to be approximated towards and separated from one another.

The angled slot of each jaw of the pair of jaws may extend in a direction transverse to the longitudinal axis of the jaw assembly. The angled slots may extend in opposed directions from one another.

In use, rotation of the actuation cable may result in rotation of the cam pin and rotation of the jaw assembly. Also, in use, axial translation of the actuation cable may result in one of approximation and separation of the pair of jaws of the jaw assembly.

The distal hub assembly may include a housing pivotally connected to the at least one support, wherein the housing may include a plurality of gear teeth defining a central axis disposed along the pivot axis.

The end effector may further include a first torque transmitting tube having a first end in meshing engagement with the plurality of gear teeth of the housing of the distal hub assembly. In use, rotation of the first torque transmitting tube may result in pivoting of the housing about the pivot axis.

The end effector may further include a rotation gear rotatably supported in the housing and pivotable about the pivot axis; a second torque transmitting tube having a first end in meshing engagement with the rotation gear; and a stem rotatably supported in and projecting from the housing, the jaw assembly being pivotally connected to the projecting portion of the stem, the stem being in meshing engagement with the rotation gear. In use, rotation of the second torque transmitting tube may result in rotation of the jaw assembly about a longitudinal axis of the stem.

The second torque transmitting tube may be rotatably disposed within a lumen of the first torque transmitting tube.

The actuation cable may extend through a lumen of the second torque transmitting tube, through the housing and through a lumen of the stem.

The pair of jaws may be pivotally supported on the stem so as to be approximated towards and separated from one another.

The angled slot of each jaw of the pair of jaws may extend in a direction transverse to the longitudinal axis of the jaw assembly. The angled slots may extend in opposed directions from one another.

In use, axial translation of the actuation cable may result in one of approximation and separation of the pair of jaws of the jaw assembly.

Further details and aspects of exemplary embodiments of the present disclosure are described in more detail below with reference to the appended figures.

BRIEF DESCRIPTION OF THE DRAWINGS

Embodiments of the present disclosure are described herein with reference to the accompanying drawings, wherein:

FIG. 3 is a perspective view of an end effector, according to another embodiment of the present disclosure, for use in the medical work station of FIG. 1A, illustrating a jaw assembly thereof in an articulated and a partially closed condition;

FIG. 4 is a further perspective view of the end effector of FIG. 3;

DETAILED DESCRIPTION

Figure 1A:
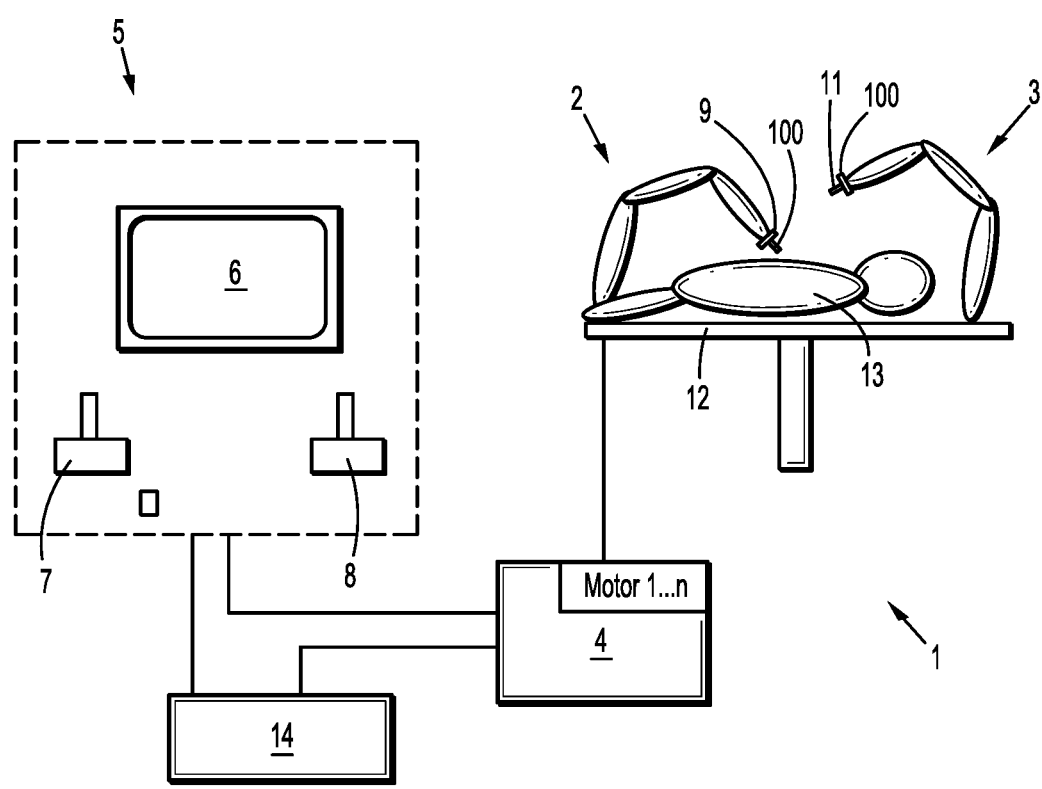
FIG. 1A is a schematic illustration of a medical work station and operating console in accordance with the present disclosure.

Embodiments of the presently disclosed jaw assemblies and/or wrist assemblies are described in detail with reference to the drawings, in which like reference numerals designate identical or corresponding elements in each of the several views. As used herein the term "distal" refers to that portion of the jaw assembly and/or wrist assembly, that is farther from the user, while the term "proximal" refers to that portion of the jaw assembly and/or wrist assembly that is closer to the user.

Figure 1B:
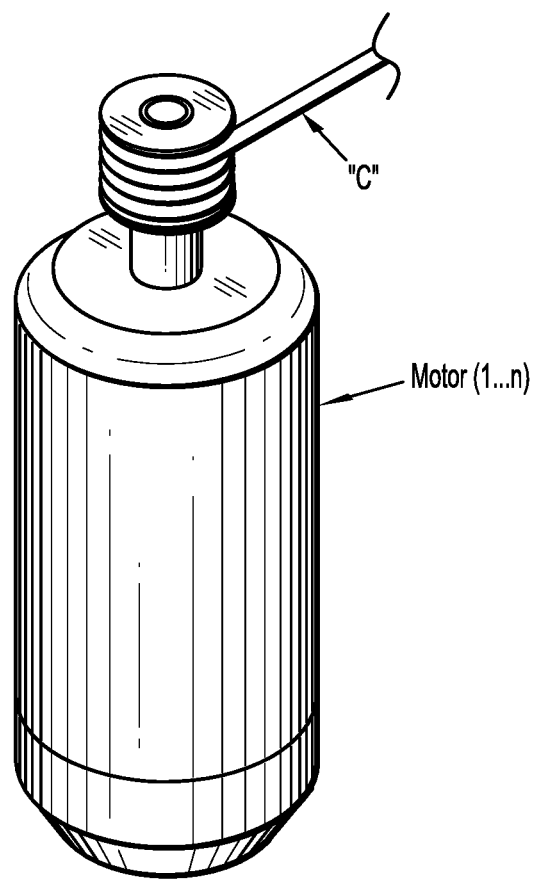
FIG. 1B is a schematic, perspective view of a motor of a control device of the medical work station of FIG. 1A.

Referring initially to FIGS. 1A and 1B, a medical work station is shown generally as work station 1 and generally includes a plurality of robot arms 2, 3; a control device 4; and an operating console 5 coupled with control device 4. Operating console 5 includes a display device 6, which is set up in particular to display three-dimensional images; and manual input devices 7, 8, by means of which a person (not shown), for example a surgeon, is able to telemanipulate robot arms 2, 3 in a first operating mode, as known in principle to a person skilled in the art.

Each of the robot arms 2, 3 includes a plurality of members, which are connected through joints, and an attaching device 9, 11, to which may be attached, for example, a surgical tool "ST" supporting an end effector 100, in accordance with any one of several embodiments disclosed herein, as will be described in greater detail below.

Robot arms 2, 3 may be driven by electric drives (not shown) that are connected to control device 4. Control device 4 (e.g., a computer) is set up to activate the drives, in particular by means of a computer program, in such a way that robot arms 2, 3, their attaching devices 9, 11 and thus the surgical tool (including end effector 100) execute a desired movement according to a movement defined by means of manual input devices 7, 8. Control device 4 may also be set up in such a way that it regulates the movement of robot arms 2, 3 and/or of the drives.

Medical work station 1 is configured for use on a patient 13 lying on a patient table 12 to be treated in a minimally invasive manner by means of end effector 100. Medical work station 1 may also include more than two robot arms 2, 3, the additional robot arms likewise being connected to control device 4 and being telemanipulatable by means of operating console 5. A medical instrument or surgical tool (including an end effector 100) may also be attached to the additional robot arm. Medical work station 1 may include a database 14, in particular coupled to with control device 4, in which are stored for example pre-operative data from living being 13 and/or anatomical atlases.

Reference may be made to U.S. Patent Publication No. 2012/0116416, filed on Nov. 3, 2011, entitled "Medical Workstation," the entire content of which is incorporated herein by reference, for a detailed discussion of the construction and operation of medical work station 1.

Control device 4 may control a plurality of motors (Motor 1 . . . n) with each motor configured to wind-up or let out a length of a cable "C" (FIG. 1B) extending through each robot arm to end effector 100 of the surgical tool, or to rotate a gear or a drive shaft (not shown). In use, as cables "C" are wound-up and let out, cables "C", gears or drive shafts may effect operation and/or movement of each end effector of the surgical tool. It is contemplated that control device 4 coordinates the activation of the various motors (Motor 1 . . . n) to coordinate a winding-up or letting out a length of a respective cable "C" in order to coordinate an operation and/or movement of a respective end effector. Although FIG. 1B shows a single cable "C" that is wound up or let out by a single motor, in some instances two or more cables or two ends of a single cable may be wound up or let out by a single motor. For example, in some instances, two cables or cable ends may be coupled in opposite directions to a single motor so that as the motor is activated in a first direction, one of the cables winds up while the other cable lets out. Other cable configurations may be used in different embodiments.

Figure 2:
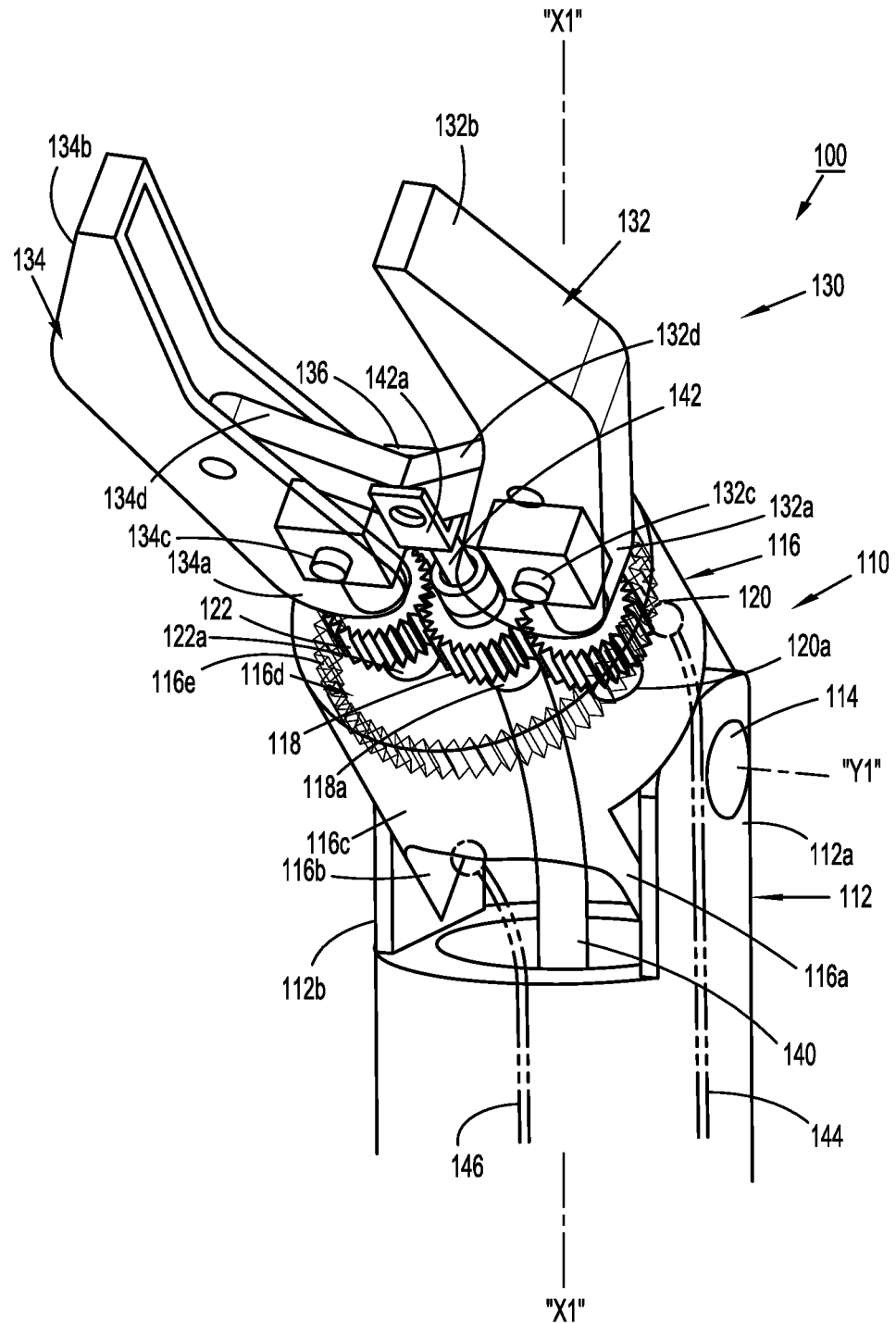
FIG. 2 is a perspective view of an end effector, according to an embodiment of the present disclosure, for use in the medical work station of FIG. 1A, illustrating a jaw assembly thereof in an articulated and an open condition.

Turning now to FIG. 2, an end effector for connection to robot arms 2, 3 and for manipulation by control device 4, is generally designated as 100. End effector 100 includes a wrist assembly 110, and a jaw assembly 130 pivotally connected to wrist assembly 110. Wrist assembly 110 includes a proximal hub 112, in the form of a distally extending clevis, defining a first longitudinal axis "X1-X1." Proximal hub 112 defines a first pivot axis "Y1-Y1" that is oriented orthogonal to the first longitudinal axis "X1-X1." In an embodiment, first pivot axis "Y1-Y1" may extend through the first longitudinal axis "X1-X1." Proximal hub 112, being in the form of a clevis, includes a pair of spaced apart, opposed upright supports 112a, 112b through which first pivot axis "Y1-Y1" extends.

Wrist assembly 110 further includes a distal hub assembly 116 pivotally connected to upright supports 112a, 112b of proximal hub 112. Distal hub assembly 116 includes a body portion 116c having a pair of spaced apart, opposed, proximally extending, upright supports 116a, 116b. Upright supports 116a, 116b of distal hub assembly 116 are pivotally connected to respective upright supports 112a, 112b of proximal hub 112, via a pivot pin 114. Pivot pin 114 is disposed along first pivot axis "Y1-Y1".

Body portion 116c of distal hub assembly 116 defines a distal bore/recess 116d including a ring of gear teeth 116e, formed in a surface thereof. The ring of gear teeth 116e taking the form of a ring gear defining a central axis.

Distal hub assembly 116 includes a spur gear 118, in the form of a sun gear, rotatably supported in bore 116d. Sun gear 118 includes an axis of rotation that is co-axial with the central axis of the ring gear 116e. Distal hub assembly 116 further includes a first spur gear 120 and a second spur gear 122, each being in the form of a planet gear, rotatably supported in bore 116d. Each planet gear 120, 122 includes an axis of rotation that is parallel with respect to the central axis of the ring gear 116e. Each of spur gears 118, 120 and 122 is supported on a respective axle, shaft or rod 118a, 120a, 122a.

With continued reference to FIG. 2, as mentioned above, end effector 100 includes a jaw assembly 130 that is pivotally supported on distal hub assembly 116. Jaw assembly 130 includes a pair of jaws 132, 134 pivotally connected, one each, to a respective shaft 120a, 122a of distal hub assembly 116. Specifically, each jaw 132, 134 includes a respective proximal end 132a, 134a pivotally connected to respective shaft 120a, 122a of distal hub assembly 116, via respective pivot pins 132c, 134c; and a respective distal end 132b, 134b.

Each jaw 132, 134 pivotally supports a respective link arm 132d, 134d that extends therefrom and extends towards one another. Free ends of the link arms 132d, 134d are pivotally connected to a connecting hub 142a that is supported on a distal end of an actuation cable 142.

In accordance with the present disclosure and the present embodiment, ring gear 116e, sun gear 118, and planet gears 120, 122 constitute a gear system that is configured and adapted to transfer/transmit rotational forces generated by motors (Motor 1 . . . n) of control device 4 into a rotation of jaw assembly 130 about a longitudinal axis of distal hub assembly 116.

End effector 100 includes a torque transmitting tube, sleeve, sheath or shaft 140 having a distal end non-rotatably connected to sun gear 118, and a proximal end (not shown) that is operatively connected to at least one of motors (Motor 1 . . . n) of control device 4. Specifically, the proximal end of tube 140 extends through robot arm 2 or 3 and is operatively connected to at least one of motors (Motor 1 . . . n) such that as the at least one of motors (Motor 1 . . . n) is activated, tube 140 is rotated along a longitudinal axis thereof. In operation, as tube 140 is rotated, said rotation is transmitted to sun gear 118. Tube 140 may be constructed from a material (e.g., stainless steel, etc.) so as to be able to transmit rotative forces.

With continued reference to FIG. 2, in operation, as sun gear 118 is rotated, due to the rotation of tube 140, said rotation is transmitted to planet gears 120, 122 to causes jaw assembly 130 to rotate, either clockwise or counter-clockwise, about the longitudinal axis of distal hub assembly 116.

In accordance with the present disclosure and the present embodiment, link arms 132d, 134d and actuation cable 142 constitute a jaw open/close system that is configured and adapted to transfer/transmit axial forces, due to operation of at least one of motors (Motor 1 . . . n) of control device 4 into an opening/closing of jaw assembly 130.

As mentioned above, end effector 100 includes a force transmitting actuation cable 142 having a distal end connected to link arms 132d, 134d via hub 142a, and a proximal end (not shown) that is operatively connected to at least one of motors (Motor 1 . . . n) of control device 4. Specifically, the proximal end of cable 142 extends through robot arm 2 or 3 and is operatively connected to at least one of motors (Motor 1 . . . n) such that as the at least one of motors (Motor 1 . . . n) is activated, cable 142 is axially translated along a longitudinal axis thereof. In operation, as actuation cable 142 is axially translated, said axial translation is transmitted to link arms 132d, 134d to either open or close jaw assembly 130. Actuation cable 142 is constructed from a material (e.g., stainless steel, etc.) so as to be able to transmit axial compressive and tensile forces.

With continued reference to FIG. 2, in operation, as link arms 132d, 134d are actuated, due to the axial translation of actuation cable 142, said actuation is transmitted to jaws 132, 134 to causes jaw assembly 130 to open or close.

In accordance with the present disclosure and the present embodiment, end effector 100 includes a pair of articulation cables 144, 146 having a respective distal end connected to distal hub assembly 116, and a proximal end (not shown) that is operatively connected to at least one of motors (Motor 1 . . . n) of control device 4. Specifically, the distal ends of articulation cables 144, 146 are connected to distal hub assembly 116 at opposed radial locations relative to pivot axis "Y1-Y1," and respective proximal ends of articulation cables 144, 146 extend through robot arm 2 or 3 and is operatively connected to at least one of motors (Motor 1 . . . n) such that as the at least one of motors (Motor 1 . . . n) is activated, articulation cables 144, 146 are axially translated in opposed directions relative to one another. In operation, as articulation cables 144, 146 are axially translated, said axial translation is transmitted to distal hub assembly 116 to either pivot distal hub assembly 116 in either a first direction or a second direction about pivot axis "Y1-Y1." Each articulation cable 144, 146 may be constructed from a material (e.g., stainless steel, etc.) so as to be able to transmit axial compressive and tensile forces.

Turning now to FIGS. 3 and 4, an end effector for connection to robot arms 2, 3 and for manipulation by control device 4, in accordance with another embodiment of the present disclosure, is generally designated as 200.

End effector 200 includes a wrist assembly 210, and a jaw assembly 230 pivotally connected to wrist assembly 210. Wrist assembly 210 includes a proximal hub 212, in the form of a distally extending clevis, defining a first longitudinal axis "X1-X1." Proximal hub 212 defines a first pivot axis "Y1-Y1" that is oriented orthogonal to the first longitudinal axis "X1-X1." In an embodiment, first pivot axis "Y1-Y1" may extend through the first longitudinal axis "X1-X1." Proximal hub 212, being in the form of a clevis, includes a pair of spaced apart, opposed upright supports 212a, 212b through which first pivot axis "Y1-Y1" extends.

Wrist assembly 210 further includes a distal hub assembly 216 pivotally connected to upright supports 212a, 212b of proximal hub 212. Distal hub assembly 216 is in the form of a turret design including an annular or cylindrical body 216a, a proximal plate 216b rotatably supported at a proximal end of cylindrical body 216a, and a distal plate 216c rotatably supported at a distal end of cylindrical body 216a. Proximal plate 216b and distal plate 216c may be connected to one another such proximal plate 216b and distal plate 216c are rotatable with respect to one another.

With continued reference to FIGS. 3 and 4, as mentioned above, end effector 200 includes a jaw assembly 230 that is pivotally supported on distal hub assembly 216, and which defines a longitudinal jaw axis "X2-X2". Jaw assembly 230 includes a pair of jaws 232, 234 pivotally connected to cylindrical body 216a of distal hub assembly 216. Specifically, each jaw 232, 234 includes a respective proximal end 232a, 234a pivotally connected to cylindrical body 216a of distal hub assembly 216 via a pivot pin 216d that is supported on cylindrical body 216a of distal hub assembly 216.

Each jaw 232, 234 includes a respective distal end 232b, 234b extending distally of pivot pin 216d. Each jaw 232, 234 defines a respective transverse cam slot 232c, 234c formed therein, wherein the cam slots 232c, 234c overlap one another.

Jaw assembly 230 includes a cam pin 236 slidably disposed within cam slots 232c, 234c. In operation, as will be discussed in detail below, as cam pin 236 translated axially, in a distal or proximal direction, relative to a longitudinal axis of jaw assembly 230, cam pin 236 acts on jaws 232, 234 to cause jaws 232, 234 to open or close.

End effector 200 includes a torque transmitting tube, sleeve, sheath or shaft 240 having a distal end non-rotatably connected to a proximal plate 216b of distal hub assembly 216, and a proximal end (not shown) that is operatively connected to at least one of motors (Motor 1 . . . n) of control device 4. Specifically, the proximal end of tube 240 extends through robot arm 2 or 3 and is operatively connected to at least one of motors (Motor 1 . . . n) such that as the at least one of motors (Motor 1 . . . n) is activated, tube 240 is rotated along a longitudinal axis thereof. In operation, as tube 240 is rotated, said rotation is transmitted to proximal plate 216b and distal plate 216c of distal hub assembly 216. As plates 216b, 216c are rotated, said rotation is transmitted to jaws 232, 234 thereby causing jaws 232, 234 to rotate about the longitudinal axis thereof. Tube 240 may be constructed from a material (e.g., stainless steel, etc.) so as to be able to transmit rotative forces.

End effector 200 also includes a force transmitting actuation cable 242 having a distal end rotatably or non-rotatably connected to cam pin 236, and a proximal end (not shown), extending through tube 240, that is operatively connected to at least one of motors (Motor 1 . . . n) of control device 4. Specifically, the proximal end of cable 242 extends through robot arm 2 or 3 and is operatively connected to at least one of motors (Motor 1 . . . n) such that as the at least one of motors (Motor 1 . . . n) is activated, cable 242 is axially translated along a longitudinal axis thereof. In operation, as actuation cable 242 is axially translated, said axial translation is transmitted to cam pin 236 to either open or close jaw assembly 230. Actuation cable 242 is constructed from a material (e.g., stainless steel, etc.) so as to be able to transmit axial compressive and tensile forces. Further, in operation, it is contemplated that as actuation cable 242 is rotated, said rotation is transmitted to cam pin 236 to rotate jaw assembly 230.

In accordance with the present disclosure and the present embodiment, end effector 200 includes a pair of articulation cables 244, 246 having a respective distal end connected to distal hub assembly 216, and a proximal end (not shown) that is operatively connected to at least one of motors (Motor 1 . . . n) of control device 4. Specifically, the distal ends of articulation cables 244, 246 are connected to cylindrical body 216a of distal hub assembly 216 at opposed radial locations relative to pivot axis "Y1-Y1," and respective proximal ends of articulation cables 244, 246 extend through robot arm 2 or 3 and is operatively connected to at least one of motors (Motor 1 . . . n) such that as the at least one of motors (Motor 1 . . . n) is activated, articulation cables 244, 246 are axially translated in opposed directions relative to one another. In operation, as articulation cables 244, 246 are axially translated, said axial translation is transmitted to distal hub assembly 216 to either pivot distal hub assembly 216 in either a first direction or a second direction about pivot axis "Y1-Y1." Each articulation cable 244, 246 may be constructed from a material (e.g., stainless steel, etc.) so as to be able to transmit axial compressive and tensile forces.

Figure 5:
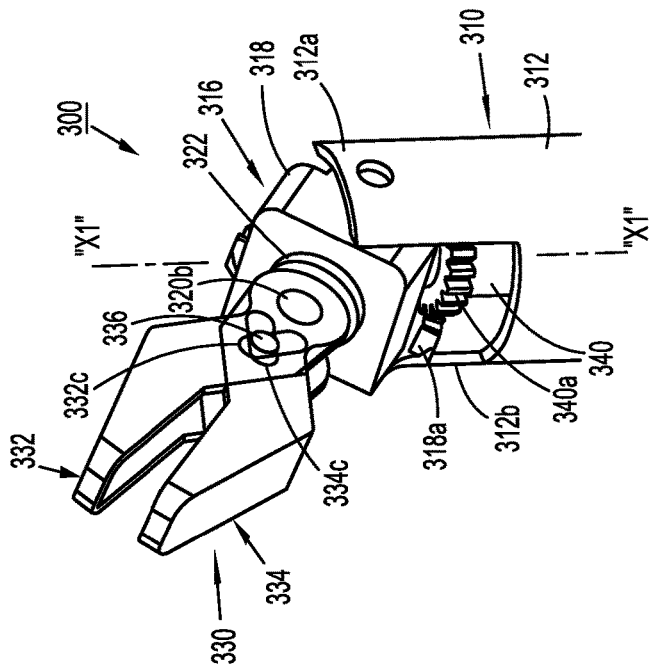
FIG. 5 is a perspective view of an end effector, according to yet another embodiment of the present disclosure, for use in the medical work station of FIG. 1A, illustrating a jaw assembly thereof in an articulated and a closed condition.
Figure 6:
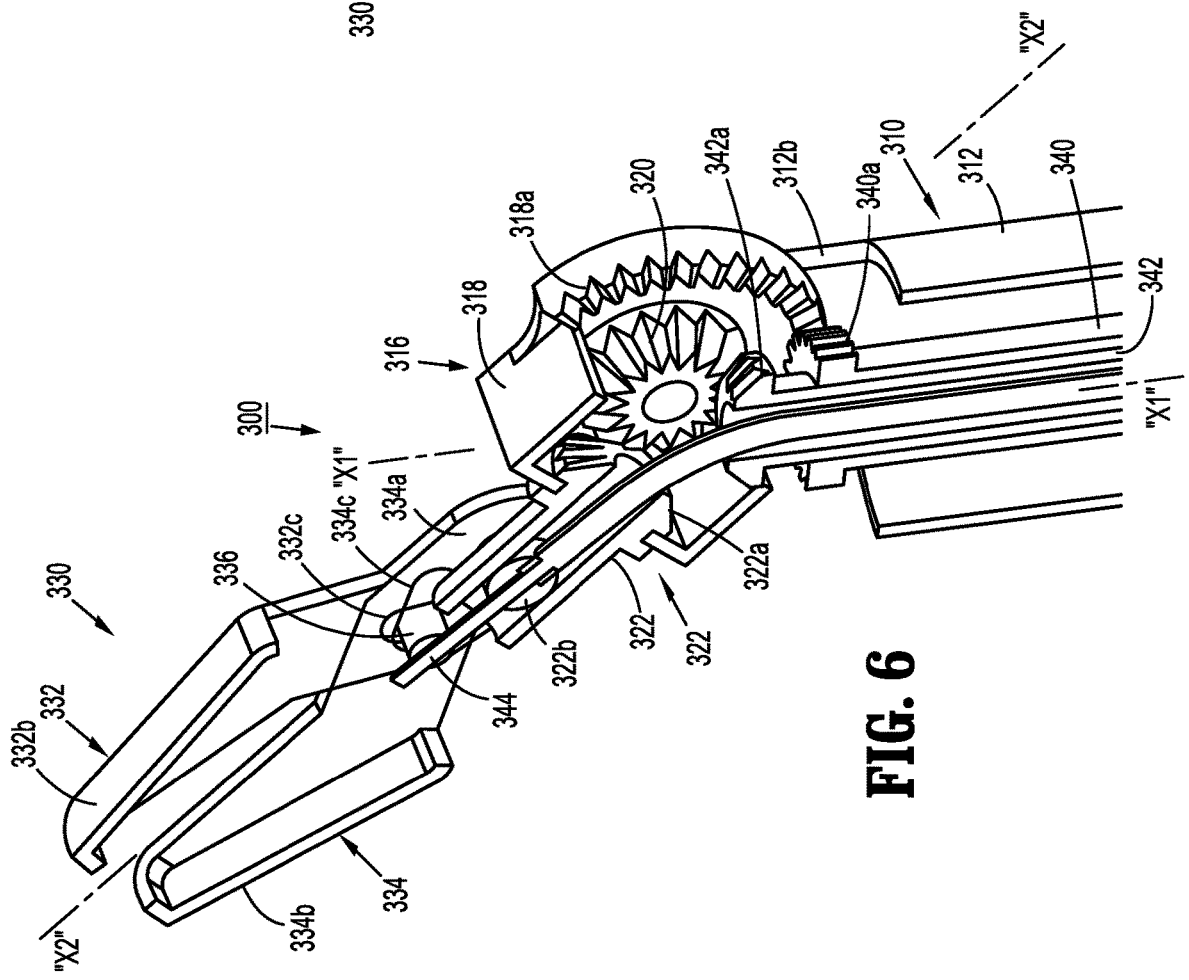
FIG. 6 is a further perspective view, with parts broken away, of the end effector of FIG. 5.

Turning now to FIGS. 5 and 6, an end effector for connection to robot arms 2, 3 and for manipulation by control device 4, in accordance with another embodiment of the present disclosure, is generally designated as 300.

End effector 300 includes a wrist assembly 310, and a jaw assembly 330 pivotally connected to wrist assembly 310. Wrist assembly 310 includes a proximal hub 312, in the form of a distally extending clevis, defining a first longitudinal axis "X1-X1." Proximal hub 312 defines a first pivot axis "Y1-Y1" that is oriented orthogonal to the first longitudinal axis "X1-X1." In an embodiment, first pivot axis "Y1-Y1" may extend through the first longitudinal axis "X1-X1." Proximal hub 312, being in the form of a clevis, includes a pair of spaced apart, opposed upright supports 312a, 312b through which first pivot axis "Y1-Y1" extends.

Wrist assembly 310 further includes a distal hub assembly 316 pivotally connected to upright supports 312a, 312b of proximal hub 312. Specifically, distal hub assembly 316 includes a housing 318 pivotally connected to upright supports 312a, 312b of proximal hub 312. Housing 318 includes a proximally extending first gear 318a (e.g., crown or bevel gear) defining a central axis that is co-incident with first pivot axis "Y1-Y1". First gear 318a includes a plurality of teeth 318b that project substantially toward first longitudinal axis "X1-X1."

Distal hub assembly 316 includes a second gear 320 (e.g., crown or bevel gear) rotatably supported in housing 318. Second gear 320 defines an axis of rotation that is coincident with first pivot axis "Y1-Y1".

Distal hub assembly 316 further includes stem 322 rotatably supported in and extending distally from housing 318. Stem 322 includes a stem gear 322a (e.g., crown or bevel gear) non-rotatably supported therein and within housing 318. Stem gear 322a is in meshing engagement with second gear 320. Stem 322 extends distally from housing 318.

With continued reference to FIGS. 5 and 6, as mentioned above, end effector 300 includes a jaw assembly 330 that is pivotally supported on distal hub assembly 316, and defines a longitudinal jaw axis "X2-X2". Jaw assembly 330 includes a pair of jaws 332, 334 pivotally connected to stem 322 of wrist assembly 310. Specifically, each jaw 332, 334 includes a respective proximal end 332a, 334a pivotally connected to stem 322 of wrist assembly 310 via a pivot pin 322b.

Each jaw 332, 334 includes a respective distal end 332b, 334b extending distally of pivot pin 322b. Each jaw 332, 334 defines a respective transverse cam slot 332c, 334c formed therein, wherein the cam slots 332c, 334c overlap one another.

Jaw assembly 330 includes a cam pin 336 slidably disposed within cam slots 332c, 334c. In operation, as will be discussed in detail below, as cam pin 336 translated axially, in a distal or proximal direction, relative to a longitudinal axis of jaw assembly 330, cam pin 336 acts on jaws 332, 334 to cause jaws 332, 334 to open or close.

End effector 300 includes a first torque transmitting tube, sleeve, sheath or shaft 340 having a distal end non-rotatably supporting a gear 340a that is in meshing engagement with first gear 318a of housing 318. First tube 340 includes a proximal end (not shown) that is operatively connected to at least one of motors (Motor 1 . . . n) of control device 4. Specifically, the proximal end of first tube 340 extends through robot arm 2 or 3 and is operatively connected to at least one of motors (Motor 1 . . . n) such that as the at least one of motors (Motor 1 . . . n) is activated, first tube 340 is rotated along a longitudinal axis thereof. In operation, as first tube 340 is rotated, said rotation is transmitted to housing 318 of distal hub assembly 316 via the meshing engagement of gear 340a and gear 318a to pivot distal hub assembly 316, and jaw assembly 330, about first pivot axis "Y1-Y1."

End effector 300 also includes a second torque transmitting tube, sleeve, sheath or shaft 342 having a distal end non-rotatably supporting a gear 342a that is in meshing engagement with second gear 320 of distal hub assembly 316. Second tube 342 includes a proximal end (not shown) that extends through first tube 340 and that is operatively connected to at least one of motors (Motor 1 . . . n) of control device 4. Specifically, the proximal end of second tube 342 extends through robot arm 2 or 3 and is operatively connected to at least one of motors (Motor 1 . . . n) such that as the at least one of motors (Motor 1 . . . n) is activated, second tube 342 is rotated along a longitudinal axis thereof. In operation, as second tube 342 is rotated, said rotation is transmitted to second gear 320 of distal hub assembly 316 which is transmitted to stem gear 322a of stem 322. As stem 322 is rotated, said rotation is transmitted to pivot pin 322b which transmits rotation to jaws 330, 332.

Tubes 340, 342 may be constructed from a material (e.g., stainless steel, etc.) so as to be able to transmit rotative forces.

End effector 200 also includes a force transmitting actuation cable 344 having a distal end rotatably or non-rotatably connected to cam pin 336, and a proximal end (not shown), extending through stem 322 and second tube 342, that is operatively connected to at least one of motors (Motor 1 . . . n) of control device 4. Specifically, the proximal end of cable 344 extends through robot arm 2 or 3 and is operatively connected to at least one of motors (Motor 1 . . . n) such that as the at least one of motors (Motor 1 . . . n) is activated, cable 344 is axially translated along a longitudinal axis thereof. In operation, as actuation cable 344 is axially translated, said axial translation is transmitted to cam pin 336 to either open or close jaw assembly 330. Actuation cable 344 is constructed from a material (e.g., stainless steel, etc.) so as to be able to transmit axial compressive and tensile forces.

In accordance with the present disclosure, end effectors that are compact in design, and yet may transmit relatively large forces or achieve a relatively large range of motion of pivoting and rotation, are contemplated and described. The gear trains disclosed herein enable transmission of relatively high loads, and may be accomplished with tight tolerances. Additionally, relatively high precision of control of movement of the end effectors is achieved.

It will be understood that various modifications may be made to the embodiments disclosed herein. For example, while the cam pulleys disclosed herein have been shown and described as being connected to the proximal ends of the jaws, it is contemplated and within the scope of the present disclosure, for the cam pulley to be operatively connected with the distal portion of the jaws. Therefore, the above description should not be construed as limiting, but merely as exemplifications of various embodiments. Those skilled in the art will envision other modifications within the scope and spirit of the claims appended thereto.

What is claimed is:

1. An end effector for use and connection to a robot arm of a robotic surgical system, wherein the end effector is controlled and/or articulated by at least one motor of a control device of the robotic surgical system, the end effector comprising:
   a wrist assembly defining a longitudinal axis, the wrist assembly including:
      at least one support; and
      a distal hub assembly including:
         a cylindrical body pivotally connected to the at least one support about a pivot axis extending transverse to a central axis of the cylindrical body; and
         a plate rotatably supported on at least one of a distal end or a proximal end of the cylindrical body;
   a jaw assembly defining a longitudinal axis and including:
      a first jaw having:
         a proximal portion operatively supported by the plate of the distal hub assembly; and
         a distal portion extending distally of the proximal portion thereof, wherein the first jaw defines a first angled slot therein; and
      a second jaw having:
         a proximal portion operatively supported by the plate of the distal hub assembly; and
         a distal portion extending distally of the proximal portion thereof, wherein the second jaw defines a second angled slot therein, wherein the first angled slot and the second angled slot cross one another; and an actuation cable having a distal end operatively connected to the first angled slot of the first jaw and the second angled slot of the second jaw via a cam pin, and a proximal end operatively connected to the at least one motor for controlling and/or articulating the end effector, wherein axial translation of the actuation cable results in one of an opening and a closing of the jaw assembly.

2. The end effector according to claim 1, further comprising a torque transmitting tube having a distal end operatively connected to the plate of the distal hub assembly and a proximal end operatively connected to a respective motor of the at least one motor, wherein rotation of the torque transmitting tube results in rotation of the jaw assembly about the longitudinal axis thereof.

3. The end effector according to claim 2, wherein the torque transmitting tube defines a lumen therethrough, and wherein the actuation cable is disposed within the lumen of the torque transmitting tube.

4. The end effector according to claim 2, wherein the cam pin is slidably disposed within the angled slots defined in each of the first jaw and the second jaw.

5. The end effector according to claim 4, wherein the jaw assembly is supported in the distal hub assembly so as to be rotatable about the central axis of the cylindrical body and pivotable about the pivot axis of the distal hub assembly.

6. The end effector according to claim 5, wherein the first jaw and the second jaw are pivotally supported in the cylindrical body so as to be approximated towards and separated from one another.

7. The end effector according to claim 4, wherein the first angled slot of the first jaw and the second angled slot of the second jaw extend in a direction transverse to the longitudinal axis of the jaw assembly, and wherein the first and second angled slots extend in opposed directions from one another.

* * * * *